United States Patent [19]

Hawkins, II

[11] Patent Number: 4,890,290

[45] Date of Patent: Dec. 26, 1989

[54] LASER LIGHT SOURCE WITH REDUCED SENSITIVITY TO OPTICAL FEEDBACK EFFECTS

[76] Inventor: Ralph T. Hawkins, II, 18455 SW. Lapaz Ct., Aloha, Oreg. 97007

[21] Appl. No.: 294,232

[22] Filed: Jan. 9, 1989

[51] Int. Cl.$^4$ ............................................. H01S 3/00
[52] U.S. Cl. ......................................... 372/33; 372/6; 372/12; 350/96.13
[58] Field of Search ..................... 372/6, 12, 33, 81; 350/96.13, 96.14, 96.17

[56] References Cited

U.S. PATENT DOCUMENTS

| | | | |
|---|---|---|---|
| 3,810,688 | 5/1974 | Ballman et al. | 350/96.14 |
| 3,877,781 | 4/1975 | Kaminow | 350/96.14 |
| 3,877,782 | 4/1975 | Kaminow | 350/96.14 |
| 4,667,331 | 5/1987 | Alferness et al. | 372/12 |

Primary Examiner—William L. Sikes
Assistant Examiner—B. R. R. Holloway
Attorney, Agent, or Firm—John Smith-Hill; Robert S. Hulse

[57] ABSTRACT

A laser light source with reduced sensitivity to optical feedback effects comprises an emitter device for emitting laser light. A body of electro-optic material is optically coupled to the emitter device for receiving and propagating light emitted by the emitter device. A time-varying electric field is established in the body of electro-optic material. Consequently, the frequency of the light emitted by the laser diode is shifted when it propagates through the body of electro-optic material.

9 Claims, 1 Drawing Sheet

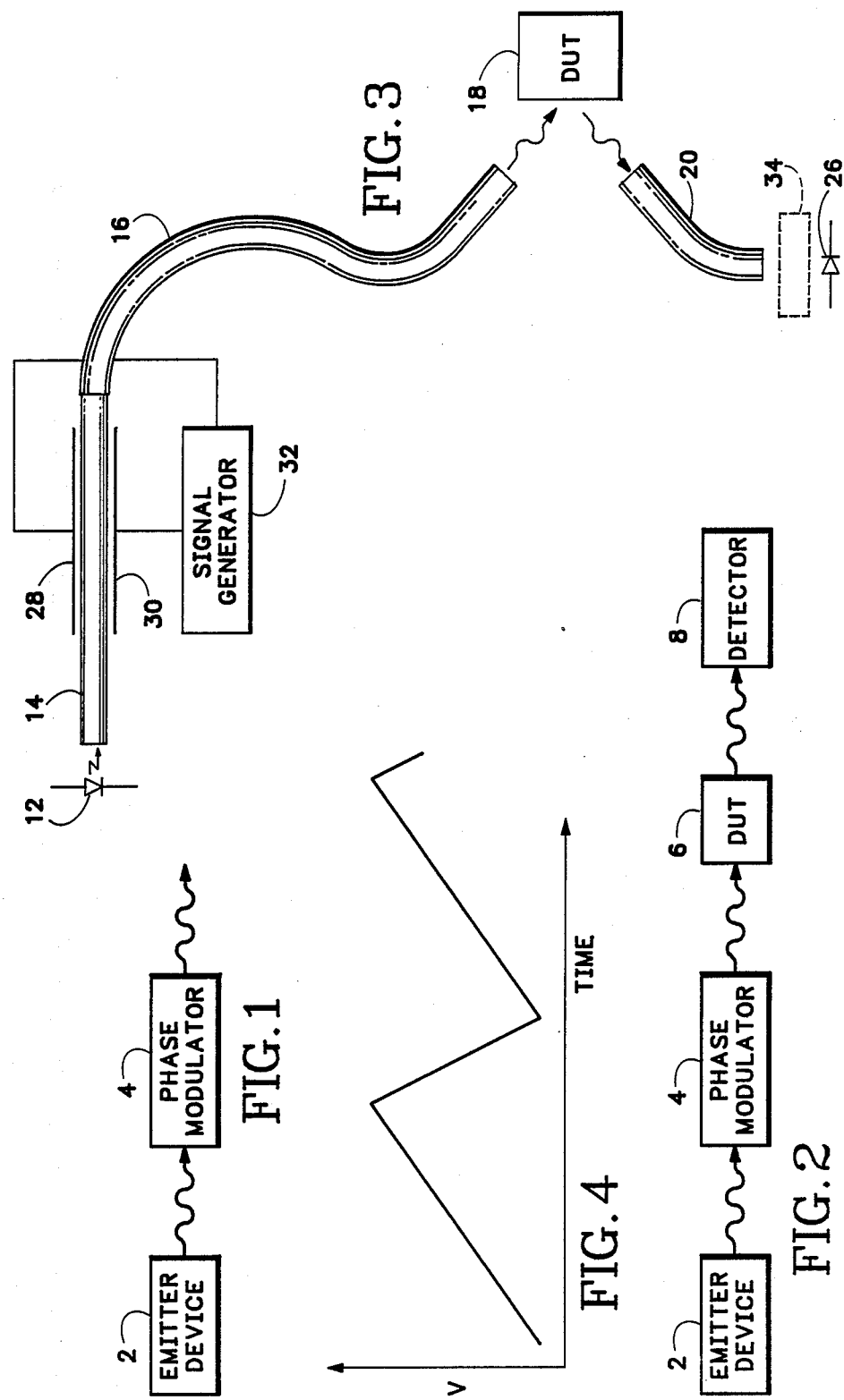

LASER LIGHT SOURCE WITH REDUCED SENSITIVITY TO OPTICAL FEEDBACK EFFECTS

BACKGROUND OF THE INVENTION

This invention relates to a laser light source with reduced sensitivity to optical feedback effects.

A laser emits light within a very narrow band of frequencies. For example, certain diode lasers that emit light at a wavelength of about 1300 nm in air, corresponding to a frequency of about 200 THz, have a line width of less than 100 MHz, or one part in about two million. When some portion of this emitted optical energy is returned to the laser, for example by reflection or scattering processes, the intensity and spectral properties of the laser emission are changed. These changes are particularly severe in the case of diode lasers, and typically have adverse effects on the system containing the laser.

As an example, the light emitted by a diode laser may be used to monitor an event by directing the light onto a transducer that reflects light with an intensity that depends on the event. A portion of the reflected light is applied to a detector, such as a photodiode, which generates a signal that depends on the intensity of the reflected light and hence contains information regarding the event. In such an arrangement, it is inevitable that some of the light emitted by the diode laser will be returned to the diode laser. For example, if an optical fiber is used to direct the light from the diode laser to the transducer, light may be reflected from the end faces of the optical fiber. Also, some of the light reflected from the transducer will be returned to the diode laser. In order to be able to extract information regarding the event from the signal generated by the detector, the intensity of the light emitted by the diode laser must be known. However, when light of frequency comparable to that emitted by the laser enters the laser, it may cause a severe perturbation in the operation of the laser, and in particular it may cause substantial variations in the intensity and spectral distribution of the light emitted by the laser. These variations make it difficult to extract useful information from the signal generated by the detector.

As a second example, light emitted by a laser may be used to excite a device under test (DUT) in some fashion, and the nature of the excitation may be dependent on the intensity and/or spectral distribution of the light incident on the DUT. If light emitted by the laser is returned to the laser and causes variations in the intensity and spectral distribution of the light emitted by the laser, this may affect the excitation of the DUT.

When light is propagated through a body of electro-optic material, and an electric field of the proper orientation exists in some portion of the electro-optic material through which the light propagates, the light undergoes a phase shift that depends on the integral with respect to propagation distance of the components of the electric field which interact with the optical field via the electro-optic effect. A particularly sensitive implementation of such an electro-optic phase shifter utilizes an optical waveguide in the body of electro-optic material. The waveguide allows confinement of the optical and electric fields in a small physical volume, thereby maximizing the strength of the interaction. For any particular choice of optical axis of propagation, the magnitude of the phase shift is unchanged by reversing the propagation direction.

SUMMARY OF THE INVENTION

A preferred embodiment of the present invention in its first aspect is a laser light source with reduced sensitivity to optical feedback effects. The light source comprises a laser device for emitting light, and a body of electro-optic material optically coupled to the laser device for receiving and propagating light emitted thereby. Electrode means are employed to establish and electric field in a region of the body of electro-optic material through which the light propagates, and a voltage source is connected to the electrode means for applying a time-varying voltage to the electrode means.

A preferred embodiment of the invention in a second aspect is apparatus for optically probing a device under test. The apparatus comprises a device for emitting laser light, and a body of electro-optic material optically coupled to the emitter device for receiving and propagating light emitted thereby and transmitting light received from the emitter device towards the device under test. Electrode means are provided for establishing an electric field in a region of the body of elelctro-optic material through which the light propagates, and a voltage source is connected to the electrode means for applying a time-varying voltage to the electrode means such that the frequency of the light applied to the device under test differs from the frequency of light emitted by the emitter device by a sufficient amount to reduce the sensitivity of the emitter device to optical feedback.

A preferred embodiment of the invention in a third aspect is a method for optically probing a device under test. The method comprises energizing an emitter device to emit laser light, propagating light emitted by the emitter device through a body of electro-optic material, applying light propagated through the body of electro-optic material to the device under test, and establishing a time-varying electric field in a region of the body of electro-optic material through which the light propagates such that the frequency of light applied to the device under test differs from the frequency of light emitted by the emitter device by a sufficient amount to reduce the sensitivity of the emitter device to optical feedback.

Preferably, the frequency difference between the light applied to the device under test and the light emitted by the emitter device is at least as great as the line width of the light emitted by the emitter device. However, this is not essential since complete insensitivity of the emitter device to optical feedback might not be required. In any event, the concept of line width of light emitted by an emitter device in a system in which optical feedback occurs is uncertain, since the feedback itself may affect the line width.

BRIEF DESCRIPTION OF THE DRAWINGS

For a better understanding of the invention and to show how the same may be carried into effect, reference will now be made, by way of example, to the accompanying drawings in which FIG. 1 is a block diagram of a laser light source having reduced sensitivity to optical feedback effects, FIG. 2 is a block diagram illustrating an application of the FIG. 1 source, FIG. 3 is a schematic diagram of apparatus for optically probing a device under test, and FIG. 4 is a graph that is used in explaining operation of the FIG. 3 apparatus.

DETAILED DESCRIPTION

The laser light source illustrated in FIG. 1 comprises an emitter device 2 that emits laser light at a frequency of, for example, 200 THz and an electro-optic phase modulator 4 that receives laser light emitted by the device 2 and imposes a phase shift on the light received from the device 2. The amount of the phase shift varies as a function of time, and the variation may be, for example, linear. The rate of change of phase of a periodic wave is the frequency of the wave. Therefore, the variation in phase shift as a function of time causes the frequency of the light leaving the phase modulator to be shifted with respect to the frequency of the light emitted by the device 2. If the phase shift varies linearly with time, the frequency shift is constant. Accordingly, the frequency of the light that is emitted from the phase modulator 4 is different from the frequency of the light emitted by the device 2. If light emitted by the phase modulator is reflected back into the phase modulator, a portion of this light will enter the emitted device. However, on passing through the phase modulator, the frequency of the light is again shifted. Since a frequency shift of more than 100 MHz can be achieved using an electro-optic phase modulator of known construction, the total frequency shift that occurs can be sufficient that the light received by the device 2 is well outside the frequency band in which the device 2 is preferentially emitting light, and therefore entry of this light into the device 2 perturbs operation of the emitter device to a significantly reduced extent.

FIG. 2 illustrates a typical application of the light source shown in FIG. 2. As shown in FIG. 2, the light emitted by the phase modulator 4 may be applied to a device under test (DUT) 6. The DUT 6 transmits light received from the phase modulator 4 but in so doing affects some property of the light in a manner that depends on an event being monitored. The light transmitted by the DUT 6 is applied to a detector 8, which is able to detect the manner in which the properties of the light have been affected by passage through the DUT 6. For example, the event being monitored might influence the intensity with which light is transmitted by the DUT, in which case the detector 8 detects the intensity of the light incident thereon. It is, therefore, important that the intensity of light emitted by the device 2 should remain substantially constant or at least should not vary in a manner that cannot be readily compensated.

Light may be reflected toward the source from the DUT or from the detector 8. Some of this reflected light will reach the emitter device 2, but when the frequency of the reflected light incident on the device 2 differs sufficiently from the frequency of the light emitted by the device, reflected light causes significantly reduced pertubation of the intensity and spectral distribution of the light emitted by the device 2.

FIG. 3 illustrates in more detail a possible implementation of the phase modulator 4 and also illustrates, in more detail than FIG. 2, a second possible application of the source.

The apparatus illustrated in FIG. 3 comprises a diode laser 12 which emits light at a frequency of, for example, 200 THz. The diode laser is coupled to an optical waveguide 14 and the waveguide is in turn coupled to an optical fiber 16 for transmitting light to a test location, at which light emitted from the fiber 16 is incident on a device under test (DUT) 18. Some of the light incident on the DUT 18 is reflected by the DUT and enters a second fiber 20. The intensity with which light is reflected by the DUT depends on an event that influences the DUT. Light reflected by the DUT is not significantly shifted in frequency relative to light incident on the DUT. Light that enters the optical fiber 20 at the test location is applied to a photodiode 26, which provides an output signal that depends on the intensity of the light incident on the photodiode.

The optical waveguide 14 is made of an electro-optic material, such as lithium niobate, and has two electrodes 28, 30 on opposite sides thereof. A signal generator 32 is connected across the electrodes 28 and 30. The signal generator 32 generates an oscillatory voltage signal. A particularly useful oscillatory signal would be one having a ramp waveform, in which case the electric field established in the waveguide varies linearly with time.

Light that passes from the diode laser 12 through the waveguide 14 is shifted in frequency due to the interaction between the electric and optical fields exiting in the waveguide. Accordingly, the frequency of the light that is emitted from the fiber 16 at the test location is different from the frequency of the light emitted by the diode laser. Also, the frequency of the light reflected from the DUT 18, being the same as the frequency of the light leaving the fiber 16, is different from the frequency of the light emitted by the diode laser. It is inevitable that some of the light reflected from the DUT will enter the fiber 16 and pass through the waveguide 14 so that it reaches the diode laser 12. When passing through the waveguide, the frequency of the light is again shifted, by the same amount and in the same sense as when it first passed through the waveguide. By appropriately selecting the rate of change of the output voltage of the signal generator 32, one can ensure that the frequency of light received by the diode laser 12 differs from the frequency of the light emitted by the diode laser by at least the line width of that light, and therefore entry of this light into the diode laser does not perturb operation of the diode laser.

Of course, it is not possible for the voltage of the ramp waveform to change indefinitely at the same rate, and the signal generator 32 must be reset periodically. It takes a finite time to reset the signal generator. The propagation time from the diode laser 12 to the DUT 18 can be such that the reflected light is propagated through the waveguide during the interval in which the signal generator is being reset. If the slope of the waveform during the reset interval is equal in magnitude but opposite in sign to the slope of the ramp waveform, the reflected light received by the diode laser will be within the line width of the diode laser, and operation of the diode laser will be perturbed. Accordingly, the signal generator is designed to provide a signal having an asymmetric waveform, a particular example of which would be a signal having an asymmetric triangle waveform, i.e., a triangle waveform in which the slope of the rising edge is not equal in magnitude to the slope of the falling edge, as shown in FIG. 4. If the diode laser emits light at a frequency $f_o$, the slope of the rising edge of the triangle waveform results in a frequency shift $F_+$, and the slope of the falling edge results in a frequency shift $F_-$, the frequency f of light returned to the laser diode is given by $$f = \begin{matrix} f_o + 2F_+ \\ f_o + F_+ + F_- \\ f_o + 2F_- \end{matrix}$$

By providing a sufficient difference between $F_+$ and $F_-$, the frequency f will never be within the line width of the diode laser.

It will be appreciated that the invention is not restricted to the particular embodiments that have been described, and that variations may be made therein without departing from the scope of the invention as defined in the appended claims and equivalents thereof. For example, the light emitted by the fiber 20 need not be incident directly on the photodiode 26 but may be processed in some fashion by a device interposed between the fiber 20 and the photodiode 26, as indicated by the device 34 shown in dashed lines in FIG. 3. The device 34 might, for example, affect the state of polarization of the light emitted by the fiber 20. Furthermore, the measurement need not be performed by detecting light reflected from the DUT, since some other effect, e.g. a photovoltaic effect, may be used to measure the effect of the light incident on the DUT. Also, although it is preferred that the electro-optic material through which the light is propagated from the emitter device be in the form of a waveguide and that the electric field be perpendicular to the direction of propagation of light through the waveguide, neither of these features is essential to the invention. In the event that the light is propagated through bulk electro-optic material, it is of course necessary that the field be established in a region of the electro-optic material through which the light propagates. It is not essential to the invention that the light emitted by the laser be shifted in frequency by a constant amount, and accordingly it is not essential that the time-varying voltage signal have a linear ramp waveform. Other emitter devices than diode lasers suffer from optical feedback effects, and the invention is applicable to reducing the sensitivity of those other devices to those effects.

I claim:

1. A laser light source with reduced sensitivity to optical feedback effects, comprising:
   a laser device for emitting light,
   a body of electro-optic material optically coupled to said laser device for receiving and propagating light emitted thereby,
   electrode means for establishing an electric field in a region of the body of electro-optic material through which the light propagates, and
   a voltage source for generating a voltage that changes linearly with time for a selected period of time, said voltage source being connected to the electrode means for applying said voltage to the electrode means.

2. A light source according to claim 1, wherein the body of electro-optic material is in the form of a waveguide.

3. A light source according to claim 1, wherein the voltage source generates a voltage that varies cyclically, increasing linearly with time at a first rate during a first part of the cycle and decreasing linearly with time at a second rate, different from said first rate, during a second part of the cycle.

4. Apparatus for optically probing a device under test, comprising:
   an emitter device for emitting laser light,
   a body of electro-optic material optically coupled to the emitter device for receiving and propagating light emitted thereby and transmitting light received from the emitter device towards the device under test,
   electrode means for establishing an electric field in a region of the body of electro-optic material through which the light propagates, and
   a voltage source connected to the electrode means for applying a time-varying voltage to the electrode means such that the frequency of light applied to the device under test differs from the frequency of light emitted by the emitter device by a sufficient amount to reduce the sensitivity of the emitter device to optical feedback, the voltage source generating a voltage that changes linearly with time for a selected period of time.

5. Apparatus according to claim 4, wherein the body of electro-optic material is in the form of an optical waveguide.

6. Apparatus according to claim 4, wherein the voltage source generates a voltage that varies cyclically, increasing linearly with time at a first rate during a first part of the cycle and decreasing linearly with time at a second rate, different from said first rate, during a second part of the cycle.

7. A method of optically probing a device under test, comprising:
   energizing an emitter device to emit laser light,
   propagating light emitted by the emitter device through a body of electro-optic material,
   applying light propagated through the body of electro-optic material to the device under test, and
   establishing an electric field that changes linearly with time for a selected period of time in a region of the body of electro-optic material through which the light propagates such that the frequency of light applied to the device under test differs from the frequency of light emitted by the emitter device by a sufficient amount to reduce the sensitivity of the emitter device to optical feedback.

8. A method according to claim 7, comprising establishing an electric field that varies cyclically.

9. A method according to claim 8, comprising establishing an electric field that varies cyclically, increasing linearly at a first rate during a first part of each cycle and decreasing linearly at a second rate, different from said first rate, during a second part of each cycle.

* * * * *

UNITED STATES PATENT AND TRADEMARK OFFICE
CERTIFICATE OF CORRECTION

PATENT NO.  : 4,890,290

DATED       : December 26, 1989

INVENTOR(S) : Ralph T. Hawkins, II

It is certified that error appears in the above-identified patent and that said Letters Patent is hereby corrected as shown below:

On the title page, item [76] should read

--Inventor: Ralph T. Hawkins, II  18485 S.W. LaPaz Court, Aloha, Oregon 97007--.

Signed and Sealed this

Sixteenth Day of April, 1991

*Attest:*

HARRY F. MANBECK, JR.

*Attesting Officer*  *Commissioner of Patents and Trademarks*